| United States Patent [19]
Wilson

[11] 3,932,623
[45] Jan. 13, 1976

[54] METHOD OF TREATING SCHIZOPHRENIA
[76] Inventor: Ian C. Wilson, c/o Dorothea Dix Hospital, Raleigh, N.C. 27601
[22] Filed: June 18, 1974
[21] Appl. No.: 480,546

[52] U.S. Cl. ............................................. 424/177
[51] Int. Cl.² ................. A61K 37/00; C07C 103/52
[58] Field of Search................... 260/112.5; 424/177

[56] References Cited
UNITED STATES PATENTS
3,341,412   9/1967   O'Hollaran et al. ................. 424/177

OTHER PUBLICATIONS
Plotnikoff et al.: Science, 178, 417–418 (1972).
Sandler et al.: Lancet 1, 612 (1973).
Kastin et al.: Lancet, 2, 740 (1972).
Prange et al.: Lancet, 2, 999 (1972).

Primary Examiner—Lewis Gotts
Assistant Examiner—Reginald J. Suyat
Attorney, Agent, or Firm—Wenderoth, Lind & Ponack

[57] ABSTRACT

An improved method of treating schizophrenia and allied conditions such as childhood schizophrenia and autism using thyrotropin releasing hormone, L-pyroglutamyl-L-histidyl-L-proline amide, or its congeners as a treating agent.

1 Claim, No Drawings

METHOD OF TREATING SCHIZOPHRENIA

The present invention relates to an improved method of treating schizophrenia.

There are a number of clinically effecitve psychopharmaceutical substances used in the treatment of schizophrenia, mainly phenothiazines, butyrophenones, and thioxanthenes. The major drawback to these medications is their partial effectiveness. These medications are generally directed towards relied of various "target symptoms," resulting in a general beneficial modification of behavior. However, the fundamental pathological personality characteristics of the disease are generally left unchanged. Acute and chronic toxic phenomena are also commonly recorded with these medications. Acute toxic phenomena may refer to many physical systems: skin rashes, hepatic and renal dysfunction, blood dyscrasias, and extrapramidal nervous system signs and symptoms have all been documented as complicating these treatments. Chronic administration of these drugs as is often required in schizophrenia, may result in irreversible toxic effects to the skin, the eyes, the cardiovascular system, and the central nervous system. Other modalities of treatment less frequently used now than formerly are insulin comatherapy and electroschock treatment. The disadvantages of these therapies are of a similar nature to that of the use of psychopharmacological substances. These treatment modalities mainly modify the clinical symptom picture without modifying the basic personality pathology. Inherent in these therapies are certain severe complications which may result in severe physical damage or perhaps death of the subject. Both of these treatments have a substantial mortality rate.

Therefore, there exists a need for an improved method of treatment of schizophrenia. The present invention provides this method.

A neurosecretory product known as "thyrotropin releasing hormone" hereinafter referred to as TRH, is an extremely useful drug and laboratory substance. TRH was previously isolated by multi-step fractionation of hypothalamic extracts. This complex isolation yielded the valuable but expensive product. It has now been established that L-pyroglutamyl-L-histidyl-L-proline amide, a synthetic product, hereinafter referred to as (pyro) glu-his-pro($NH_2$) exhibits the same chemical and hormonal properties as the porcine TRH (Folkers et al., Biochem. and Biophys. Research Comm. 39; No. 1: 110–113, 1970). See also U.S. Pat. No. 3,737,549. The scientific community now has reached the conclusion that native TRH is chemically L-pyroglutamyl-L-histidyl-L-proline amide.

We have now found that when 100–1000 mcg. TRH or (pyro) glu-his-pro($NH_2$) is administered to schizophrenics that remarkably beneficial changes occur in these subjects in the spheres of thought, affect and behavior.

The subjects to be treated with this substance are diagnostically well-defined cases of schizophrenia presenting with classical schizophrenic symptomatology: autistic thinking, thought retardation, thought blocking, hallucinations, delusions, flattened affect, and socially withdrawn behavior. Within one to three hours after intravenous administration of TRH or (pyro) glu-his-pro($NH_2$), 100–1000 mcg. improvement in all areas of psychopathology occurs. The thought processes become more lucid and realistic with an increase in spontaneity of verbal expression. The subjects themselves remark about the sudden clarity of their thinking. Hallucinatory phenomena disappear and the subjects speak with insight about their previously disturbed perceptions. Concomitant changes in affect occur. There is an elevation in mood with a remarkable spontaneity in emotional expression. The subjects show a newly acquired emotional warmth. These beneficial effects continue for a period of several days before gradual regression with a recurrence of schizophrenic symptomatology. However, in no cases to date has the regression been complete.

The improvement in intensity of symptomatology and the "normalization" of personality characteristics make TRH or (pyro) glu-his-pro($NH_2$) particularly useful agents in the treatment of schizophrenia.

The active ingredients useful in the practice of this invention can be formulated into various pharmaceutical dosage forms such as tablets, capsules, pills, sterile aqueous or nonaqueous solutions for parenteral injection administration, and the like, for immediate or sustained release, by combining one or more of the active compounds with suitable pharmaceutically acceptable carrier or diluents according to methods, well known in the art. Such dosage forms may additionally include excipients, binders, fillers, flavoring and sweetening agents and other therapeutically inert ingredients necessary in the formulation of the desired pharmaceutical preparation.

The following examples are illustrative of suitable dosage formulations useful in the practice of this invention.

EXAMPLE 1

Tablets containing 400 mcg. TRH and having the following composition are prepared according to methods well known in the art.

| TRH | mcg. | 400 |
|---|---|---|
| Starch | mg. | 20 |
| Colloidal silica | mg. | 4 |
| Magnesium stearate | mg. | 1 |

EXAMPLE 2

Ampoules for intravenous use are prepared containing 200 mcg. of (pyro) glu-his-pro($NH_2$) in 1 ml. of sterile physiologic saline.

For purposes of the present invention there may be used not only TRH or (pyro) glu-his-pro($NH_2$) in the treatment of schizophrenia but also the use of congeners and derivatives thereof is contemplated, and such materials are deemed to be the equivalents of the parent materials. It has been shown that certain congeners of TRH, like the parent substance, antagonize the actions of pentobarbital in mice.

What is claimed is:

1. A method for the treatment of a patient suffering from schizophrenia which comprises the administration to the said patient of a therapeutically effective amount of TRH or L-pyroglutamyl-L-histidyl-L-proline amide.

* * * * *